United States Patent [19]

Yamamoto et al.

[11] Patent Number: 5,155,252
[45] Date of Patent: Oct. 13, 1992

[54] MATERIAL FOR DENTISTRY

[75] Inventors: Naoki Yamamoto; Nobuhiro Mukai; Hitoshi Ige; Masao Kobayashi; Junko Atarashi, all of Otake, Japan

[73] Assignee: Mitsubishi Rayon Co., Ltd., Tokyo, Japan

[21] Appl. No.: 564,878

[22] Filed: Aug. 9, 1990

[30] Foreign Application Priority Data

Aug. 14, 1989 [JP] Japan .................................. 1-207880
Jan. 8, 1990 [JP] Japan ...................................... 2-1373
Jan. 8, 1990 [JP] Japan ...................................... 2-1374
May 25, 1990 [JP] Japan .................................. 2-136351

[51] Int. Cl.$^5$ ............................................. C07C 51/00
[52] U.S. Cl. ..................................... 560/190; 560/205;
523/116; 523/118; 526/316; 526/320; 526/321
[58] Field of Search ................ 523/118, 116; 560/205, 560/190; 526/320, 321, 316

[56] References Cited

U.S. PATENT DOCUMENTS 4,674,980 6/1987 Ibsen et al. ............................ 523/116
4,782,100 11/1988 Iwamoto et al. ..................... 522/120

OTHER PUBLICATIONS

Patent Abstracts of Japan, vol. 8, No. 225, C-247, 16 Oct. 1984; attached.

Primary Examiner—Paul R. Michl
Assistant Examiner—LaVonda R. DeWitt
Attorney, Agent, or Firm—Cushman, Darby & Cushman

[57] ABSTRACT

A material for dentistry having a low odor, a low stimulation and a proper dough stage time is here disclosed which is prepared by blending a monomer selected from the group consisting of (meth)acrylate compounds represented by the general formula $$H_2C=\underset{\underset{\text{}}{|}}{\overset{R_1}{C}}-\underset{\underset{O}{\|}}{C}-O-X$$

(wherein X is $-R_2-O-R_3$, $$-R_5-\underset{\underset{O}{\|}}{C}-R_6 \text{ or}$$

$$-R_8-O-\underset{\underset{O}{\|}}{C}-R_9-\underset{\underset{O}{\|}}{C}-O-R_{10},$$

$R_1$ is a hydrogen atom or a methyl group, each of $R_3$, $R_6$ and $R_{10}$ is an alkyl group, and each of $R_2$, $R_5$, $R_8$ and $R_9$ is an alkylene group) and (meth)acrylate dimers.

12 Claims, 3 Drawing Sheets

MATERIAL FOR DENTISTRY

BACKGROUND OF THE INVENTION (a) Field of the Invention

The present invention relates to a material for dentistry in which a specific (meth)acrylate compound is blended.

(b) Description of the Related Prior Art

In recent years, many materials for dentistry comprising synthetic polymers have been developed, and some of them take the form of compositions each comprising monomers, a polymerization initiator and other components which can be polymerized and cured when used. Examples of such compositions include (1) crown restoration materials such as chemically polymerizable and photopolymerizable composite resins and quick-curing resins (fast-polymerizable resins), (2) adhesive and transitory adhesives, for example, between a composite resin and a tooth, between a metal and a tooth, and between teeth, (3) chemically polymerizable and photopolymerizable pit and fissure sealants, (4) artificial crown materials such as thermally polymerizable and photopolymerizable hard crown resins, (5) transitory crown materials such as polycarbonate crowns and fast-setting resins for crowns, (6) denture plate materials such as thermally polymerizable, cold polymerizable (inclusive of casting type) and injection-moldable acrylic resins and adhesive denture plate reins, (7) restoration materials such as denture plate lining agents and restoration fast-setting resins, and (8) impression materials such as agar, alginates, polysulfide rubbers, silicone rubbers and (meth)acrylic impression materials.

Among these materials, for example, as the composite resin or the hard crown resin, there is used a blend of at least one monofunctional monomer, at least one polyfunctional monomer, an inorganic filler and a radical polymerization initiator, and as the crown resin, the sealant or the adhesive, there is used a combination of at least one monofunctional monomer, at least one polyfunctional monomer and a radical polymerization initiator. Furthermore, a restoration material such as the denture plate, the denture plate lining agent and the restoring quick polymerizable resin is required to be colorless and transparent, to be easily colored, to be aesthetic and to be excellent in workability, and therefore as this kind of restoration material, there is used a mixture of a polymer component (which is in the state of a powder in most cases) such as polymethyl methacrylate (hereinafter referred to as "PMMA") and polyethyl methacrylate (hereinafter referred to as "PEMA"), at least one monofunctional monomer, at least one polyfunctional monomer and a radical polymerization initiator.

Examples of the above-mentioned monofunctional monomer component include methyl methacrylate (MMA), ethyl methacrylate (EMA), butyl methacrylate (BMA), 2-hydroxyethyl methacrylate (HEMA) and $H_2C=C(CH_3)COOC_2H_4OCOC_2H_5$. Examples of the polyfunctional monomer component include 1,6-hexanediol dimethacrylate (HD), ethylene glycol dimethacrylate (1G), triethylene glycol dimethacrylate (3G), bisphenol A diglycidyl dimethacrylate (Bis-GMA), trimethylolpropane trimethacrylate (TMPT) and dipentaerythritol pentaacrylate (2P5A).

In addition, in Japanese Laid-open Patent Publication No. 1987-178502, a material for dentistry is described which contains, as the main component, a diester compound represented by $CH_2=CR_1COOR_2OCOR_3$ (wherein $R_1$ is a hydrogen atom or an alkyl group, $R_2$ is an alkylene group and $R_3$ is an alkyl group).

However, the composite resin, the hard crown resin, the quick-curing crown resin, the sealant and the adhesive are required to be (1) free from a strong foul odor, since they are directly put in a mouth. Furthermore, they are required to be free from irritation to a skin and a mucous membrane, since they are often brought into contact with dental pulp in pits of teeth. In addition, they must maintain strength under circumstances in a mouth, since they remain in the mouth for a long period of time after curing, and from this viewpoint, (3) polymers having high water absorption properties are inconvenient.

Moreover, the restoration materials such as the denture plate and the denture plate lining agent are required to be (1) free from a strong foul odor and (2) free from irritation to a skin and a mucous membrane, since they are manipulated by hands of a dentist or a dental technician, or since they are directly brought into contact with an oral mucous membrane for the sake of molding.

However, the above-mentioned monomers inconveniently cannot meet all of these requirements (1) to (3).

For example, monomers such as MMA, EMA, BMA, HEMA, HD, 1G, 3G, TMPT and 2P5A cannot meet the above-mentioned requirements (1) and (2), and monomers such as $H_2C=C(CH_3)COOC_2H_4OCOC_2H_5$ and Bis-GMA cannot meet the above-mentioned requirements (3). Even if these monomers are combined, all of the aforesaid requirements cannot be satisfied. Therefore, the development of a composition by which these problems are solved is desired.

The diester compounds described in the above Japanese Laid-open Patent Publication No. 1987-178502 are excellent in point of less stimulation, but they have perceptibly high water absorption properties. In consequence, their strength tends to deteriorate when they are used as dental materials, and what is worse, they are liable to color.

In the case of the above restoration material, a monomer component is mixed with a polymer component at a suitable ratio, and the mixture is then placed in a predetermined mold or put in a mouth for the sake of molding. Afterward, the material is taken out therefrom, and then polymerized at room temperature or under heating, thereby obtaining the restoration material. However, in the course of this molding, it is important that the material takes the state of the so-called dough stage for a suitable period of time. In short, the composition which is free from a strong foul odor and less irritant and which has a suitable period for dough stage is demanded.

SUMMARY OF THE INVENTION

In view of such situations, the present inventors have intensively researched to solve the above-mentioned problems, and as a result, they have found that in a material for dentistry comprising a composition of monomers and a radical polymerization initiator which will be polymerized and cured when used, the monomer components are specific (meth)acrylate monomers which are less odorous and less stimulative, the water absorption of a polymer made therefrom is low, and a suitable period for dough stage is present. Thus, the present invention has been achieved on the basis of such a knowledge.

That is, the gist of the present invention resides in a material for dentistry which is prepared by blending one or more monomers selected from the group consisting of a (meth)acrylate compound represented by the general, formula (1)

(wherein $R_1$ is a hydrogen atom or a methyl group, $R_2$ is an alkylene group having 1 to 15 carbon atoms, and $R_3$ is an alkyl group having 1 to 15 carbon atoms), a (meth)acrylate compound represented by the general formula (2)

(wherein $R_4$ is a hydrogen atom or a methyl group, $R_5$ is an alkylene group having 1 to 15 carbon atoms, and $R_6$ is an alkyl group having 1 to 15 carbon atoms), a (meth)acrylate compound represented by the general formula (3)

(wherein $R_7$ is a hydrogen atom or a methyl group, $R_8$ is an alkylene group having 1 to 15 carbon atoms, $R_9$ is an alkylene group having 1 to 10 carbon atoms, and $R_{10}$ is an alkyl group having 1 to 15 carbon atoms), and a (meth)acrylate dimer represented by the formula (4), The material for dentistry containing the specific (meth)acrylate compound according to the present invention is less odorous and less irritant and has a lower water absorption as compared with conventional materials, and when used as the restoration material, it has a suitable period for dough stage. That is, in the direct treatment of the interior in the mouth of a patient by the use of the above-mentioned material, the patient can get rid of discomforts such as odor and irritation, and the curable material itself can be used for a long period of time even under severe wet conditions in the mouth, because of a less water absorption and thus an excellent dimensional stability, and because of an excellent strength, a high color stability and a good durability. In addition, the material of the present case leads to improvements of safety and sanitation for a dentist or a dental technician, and operational efficiency.

Therefore, it is fair to say that the material of the present invention has a extremely high practical value in the dental field.

DETAILED DESCRIPTION OF THE INVENTION

Now, the present invention will be described mainly about cases where a material of the present case is used as restoration materials. However, the material for dentistry of the present invention should not be limited to the restoration materials but can be suitably used as dental composite resins, crown resins, dental sealant, dental adhesives and the like.

Any compound represented by the general formula (1) can be used, so long as in the formula, $R_1$ is a hydrogen atom or a methyl group, $R_2$ is an alkylene group having 1 to 15 carbon atoms, and $R_3$ is an alkyl group having 1 to 15 carbon atoms. However, considering desired requirements of the material for dentistry such as a low odor, a low irritation, a low water absorption and a high mechanical strength of an obtained polymer, and a proper period for dough stage which is necessary in the case that the material is used as the binary restoration material, $R_2$ in the general formula (1) is an alkylene group having 1 to 15 carbon atoms but it may be a straight-chain methylene group or polymethylene group or a polymethylene group having a side chain. The $R_2$ group preferably has 1 to 7 carbon atoms. Furthermore, for the same reason, the $R_3$ in the general formula (1) is an alkyl group preferably having 1 to 7 carbon atoms. Accordingly, examples of the (meth)acrylate compound which can be particularly preferably used in the present invention are as follows:

The (meth)acrylate compound represented by the above-mentioned general formula (1) of the present invention can be prepared from a specific unsaturated carboxylic acid [$CH_2=C(R_1)-COOH$] or its acid halide and an ether alcohol ($HO-R_2-O-R_3$) by an esterification reaction or alternatively by an ester exchange reaction between the unsaturated carboxylates.

Similarly, considering the desired requirements of the material for dentistry, the alkyl group represented by the $R_4$ in the general formula (2) preferably has 1 to 7 carbon atoms, more preferably 1 to 4 carbon atoms. For the same reason, the $R_5$ in the general formula (2) is an alkylene group but it may be a straight-chain methylene group or polymethylene group or a polymethylene group having a side chain. The $R_5$ group preferably has 1 to 10 carbon atoms, more preferably 1 to 7 carbon atoms. Furthermore, for the same reason, the $R_6$ in the general formula (2) is an alkyl group preferably having 1 to 10 carbon atoms, more preferably 1 to 7. Accordingly, examples of the (meth)acrylate compound represented by the general formula (2) which can be particularly preferably used in the present invention are as follows:

-continued

-continued and

The (meth)acrylate compound represented by the above-mentioned general formula (2) regarding the present invention can be prepared by an esterification reaction between a specific unsaturated carboxylic acid [$CH_2=C(R_4)$—COOH] or its acid halide and a keto-alcohol [HO—$R_5$—C(O)—$R_6$] or alternatively by an ester exchange reaction between unsaturated carboxylates.

Similarly, considering the desired requirements of the material for dentistry, each of $R_8$ and $R_9$ in the general formula (3) is an alkylene group but it may be a straight-chain methylene group or polymethylene group or a polymethylene group having a side chain. $R_8$ group preferably has 1 to 10 carbon atoms, more preferably 1 to 6 carbon atoms. For the same reason, $R_9$ group preferably has 1 to 7 carbon atoms, more preferably 1 to 4 carbon atoms. Furthermore, for the same reason as described above, $R_{10}$ in the general formula (3) is an alkyl group preferably having 1 to 10 carbon atoms, more preferably 1 to 7. On this account, typical examples of the (meth)acrylate compound represented by the general formula (3) which can be particularly preferably used in the present invention are as follows:

The (meth)acrylate compound represented by the above-mentioned general formula (3) regarding the present invention can be prepared by an esterification reaction between a specific unsaturated carboxylic acid [$CH_2$=C($R_7$)—COO—$R_8$—OCO—$R_9$—COOH] and an alkyl alcohol ($R_{10}$—OH), or alternatively by another reaction such as a reaction of an unsaturated alcohol [$CH_2$=C($R_7$)—COO—$R_8$—OH] and an ester group-containing carboxylic acid (HOCO—$R_9$—COO—$R_{10}$), a reaction of an unsaturated carboxylic acid [$CH_2$=C($R_7$)—COOH] and an ester group-containing alcohol (HO—$R_8$—OOC—$R_9$—COO—$R_{10}$), a reaction in which the above-mentioned carboxylic acid is replaced with a carboxylic acid halide, or an ester exchange reaction between unsaturated carboxylates.

On the other hand, the methacrylate dimer represented by the general formula (4) regarding the present invention can be prepared by heating methyl methacrylate at a high temperature in the presence of a polymerization inhibitor or alternatively by fractionating a by-product formed at the time of the manufacture of methyl methacrylate.

In manufacturing the material for dentistry of the present invention, a combination of one or more kinds of monomers selected only from the above-mentioned group can be used, but it is also possible to blend another monomer component therewith, if necessary, which is polymerizable with the specific (meth)acrylate compound represented by the general formula (1), (2) or (3) or the specific methacrylate dimer represented by the formula (4), so long as the low odor and the low irritation can be maintained.

Typical examples of such another kind of monomer include 2-ethylhexyl (meth)acrylate, lauryl (meth)acrylate, tridecyl (meth)acrylate, stearyl (meth)acrylate, cyclohexyl (meth)acrylate, n-hexyl (meth)acrylate, tetrahydrofurfuryl (meth)acrylate, ethylene glycol di(meth)acrylate, diethylene glycol di(meth)acrylate, triethylene glycol, di(meth)acrylate, tetraethylene glycol di(meth)acrylate, pentaethylene glycol di(meth)acrylate, hexaethylene glycol di(meth)acrylate, heptaethylene glycol di(meth)acrylate, octaethylene glycol di(meth)acrylate, nonaethylene glycol di(meth)acrylate, 1,3-butylene glycol di(meth)acrylate, propylene glycol di(meth)acrylate, 1,3-butanediol di(meth)acrylate, 1,4-butanediol di(meth)acrylate, 1,5-pentanediol di(meth)acrylate, 1,6-hexanediol di(meth)acrylate, 1,7-heptanediol di(meth)acrylate, 1,8-octanediol di(meth)acrylate, 1,9-nonanediol di(meth)acrylate, 1,10-decanediol di(meth)acrylate, neopentyl glycol di(meth)acrylate, 2,2-bis(4-methacryloyloxyphenyl)propane, 2,2-bis(4-methacryloyloxyethoxyphenyl)propane, 2,2-bis(4-methacryloyloxypolyethoxyphenyl)propane, 2,2-bis[4-(3-methacryloyloxy-2-hydroxypropoxy)phenyl]propane, di(methacryloyloxyethyl)trimethylhexamethylenediurethane, tetramethylolmethane tri(meth)acrylate, trimethylolpropane tri(meth)acrylate, trimethylolethane tri(meth)acrylate and tetramethylolmethane tetra(meth)acrylate. They can be used singly or in combination. Above all, polyfunctional methacrylates such as ethylene glycol dimethacrylate, triethylene glycol dimethacrylate, 1,6-hexanediol dimethacrylate, 2,2-bis(4-methacryloyloxyethoxyphenyl)propane, neopentyl glycol dimethacrylate and trimethylolpropane trimethacrylate are preferable as the other copolymerizable monomer, components in view of mechanical strength of cured materials which will be obtained.

The blend ratio of the (meth)acrylate compound represented by the general formula (1), (2) or (3) or D-MMA to the above-mentioned other copolymerizable monomer component depends upon the degree of the irritation of the other copolymerizable monomer component, and usually it can be selected suitably, so long as odor and irritation are maintained at a low level. Nevertheless, the above-mentioned blend ratio is such that the amount of the (meth)acrylate compound represented by the general formula (1), (2) or (3) or D-MMA is preferably not less than 20% by weight, more preferably not less than 30% by weight.

In the case that the material for dentistry of the present invention is used as a restoration material, an organic polymer may be used which can be dissolved or swelled in the above-mentioned monomer. Typical examples of the organic polymer include polymethyl methacrylate (PMMA), polyethyl methacrylate (PEMA), MMA/EMA copolymer, MMA/BMA copolymer, polystyrene, polybutyl methacrylate, MMA/styrene copolymer, EMA/BMA copolymer, EMA/styrene copolymer, polyacrylonitrile, styrene/acrylonitrile copolymer, styrene/acrylonitrile/butadiene copolymer, polycarbonate resin, polyvinyl chloride, polyacrylates, polymethacrylates, polyester resins, polyethylene, resin, polypropylene resin, silicone resins and fluorine-containing resin. Above all, preferable are PMMA, PEMA, MMA/EMA copolymer, MMA/BMA copolymer, polystyrene, polybutyl methacrylate, MMA/styrene copolymer, EMA/BMA copolymer, EMA/styrene copolymer, and mixtures of these polymers and other polymers, because they have a particularly proper solubility.

Any particular restriction is not put on the molecular weight and the average particle diameter of this kind of polymer, but considering its solubility in the monomer component of the present invention and swell characteristics and mechanical strength of cured materials which will be obtained therefrom, the molecular weight of the polymer is preferably from 10,000 to 1,500,000, more preferably from 50,000 to 1,000,000, and the particle diameter of the polymer is preferably from 1 to 150 $\mu$m, more preferably from 10 to 100 $\mu$m.

The blend ratio of the polymer component to all the monomer components can be selected from an extensive range, but in view of the mechanical strength of the cured articles and the like, the amount of all the monomer components with respect to 10 parts by weight of the polymer component is preferably from 1 to 140 parts by weight (in other words, from 7.1 to 1,000 parts by weight with respect to 100 parts by weight of all the, monomers), more preferably from 2 to 110 parts by weight, most preferably from 4 to 85 parts by weight.

As a polymerization initiator used to obtain composite resins and restoration materials and as a curing agent used in the adhesive, there can be employed known compounds. In the case that heat curing is carried out, a substance which can thermally decompose and then initiate polymerization is used. Examples of such a substance include benzoyl peroxide, cumene hydroperoxide, t-butyl hydroperoxide, dicumyl peroxide, acetyl peroxide, lauroly peroxide and azobisisobutyronitrile. Furthermore, in the case that polymerization/curing is carried out at ordinary temperature, there can be used, for example, a combination of a peroxide and an amine, a peroxide and a sulfinic acid, or a peroxide and a cobalt compound. When the polymerization initiators are used in combination, the composition may be divided into two parts, and one part of the composition may be blended with the peroxide and the other part may be blended with the amine, the sulfinic acid or the cobalt compound. The amount of the above-mentioned curing agent is preferably from 0.01 to 15% by weight, more preferably from 0.05 to 10% by weight, most preferably from 0.1 to 7% by weight with respect to the amount of the total monomers.

In the case that polymerization/curing is carried out by means of the irradiation of ultraviolet light, or visible light, any of known photosensitizers can be used. Examples of the suitable photosensitizer include benzoin alkyl ethers such as benzoin methyl ether, benzoin ethyl ether and benzoin propyl ether, $\alpha$-diketones such as benzil, biacetyl and camphorquinone, and benzophenones such as benzophenone and methoxybenzophenone. When the above-mentioned photocuring means is employed, a reducing agent can be used in addition to the photosensitizer. Examples of the suitable reducing agent include amines such as aminobenzoic acid ester, toluidine, benzylamine and amino methacrylate.

The amount of the photocuring agent to be used is preferably from 0.01 to 15% by weight, more preferably from 0.05 to 10% by weight, most preferably from 0.1 to 7% by weight.

In the present invention, an inorganic filler can be additionally blended with the above-mentioned monomers, polymer component and polymerization/curing agent. Typical examples of the inorganic filler include oxides, hydroxides, chlorides, sulfates, sulfites, carbonates, phosphates, silicates and borates of elements in the groups I, II, III and IV of the periodic table and transition metals, mixtures thereof, and composite salts thereof. Typical examples of the inorganic filler include silicon dioxide, quartz powder, aluminum oxide, titanium oxide, barium sulfate, talc, glass powder, glass beads, glass fiber, a glass filler containing a barium salt or a strontium salt, silica gel, colloidal silica, carbon fiber, zirconium oxide, tin oxide and ceramic powder. The filler may be an untreated filler, a filler the surface of which is treated with a silane coupling agent or a titanate coupling agent, a filler coated with a polymer, or a filler composite containing an organic material prepared by the process described in Japanese Laid-open Patent Publication No. 1985-81116.

The amount of the filler is preferably from 0.1 to 630% by weight (6.3 times), more preferably from 1 to 570% by weight, most preferably from 10 to 460% by weight with respect to the amount of the total monomers.

As a molding method, any of known molding techniques can be utilized which are compression molding, cast molding and injection molding.

In the material for dentistry of the present invention, a colorant, a polymerization inhibitor, an ultraviolet absorber, an oxidation stabilizer and the like can be further blended, if necessary.

The material for dentistry of the present invention can also be used as a dental material other than the restoration material.

For example, the material for dentistry can, be utilized as an adhesive or a sealant, which can be prepared from the (meth)acrylate compound represented by the general formula (1), (2) or (3) or D-MMA of the present invention, the same other monomer component copolymerizable with this compound as in the case of the above-mentioned restoration material, a polymerization initiator, and if necessary, a polymer, an inorganic filler, a colorant, a polymerization inhibitor, an ultraviolet absorber, an oxidation stabilizer and the like.

In addition, the material for dentistry of the present invention can also be utilized as a composite resin, a hard crown resin or a quick-curing crown resin, which can be prepared from the (meth)acrylate compound represented by the general formula (1), (2) or (3) or D-MMA of the present invention, the same other monomer component copolymerizable with this compound as in the case of the above-mentioned restoration material, a polymerization initiator, an inorganic filler, and the like. This inorganic filler is the same as used in the restoration material. If necessary, a polymer, a colorant, a polymerization inhibitor, an ultraviolet absorber, an oxidation stabilizer and the like can also be blended therewith.

Now, the present invention will be described in reference to examples.

The (meth)acrylate compound of the present invention 5 is not different at all from a conventional (meth)acrylate monomer for dentistry in point of reactivity except for being less odorous and less irritant.

Thus, in the following examples, reference will be made mainly to embodiments of restoration materials.

EXAMPLES 1 TO 8 AND COMPARATIVE EXAMPLES 1 to 4

As specific (meth)acrylate compounds represented by the general formula (1) according to the present invention, the following compounds were used, and an odor test, an irritation test and a polymer solubility test were then carried out.

Procedures of the respective tests will be briefly described hereinafter, and the results of the tests will be set forth together in Table 1.

Odor Test

Five unspecified testers aged 20 to 30 were selected, and the odor test was carried out in accordance with the following evaluation criterion by them. When the testers had different evaluations, the test was repeated again, until three or more of the testers had the same evaluation.

Evaluation Criterion
○. . . faintly odorous
△. . . weakly odorous
X. . . strongly odorous

Irritation Test

Five unspecified testers aged 20 to 30 were selected. One drop of a sample was dropped on the tongue tip of each tester, and after one minute, evaluation was made on the basis of the pain of the tongue tip in accordance with the following evaluation criterion.

Evaluation Criterion
○. . . little painful
△. . . slightly painful
X. . . very painful

Polymer Solubility Test

A polyethyl methacrylate powder having an average molecular weight of $230 \times 10^3$ and an average particle diameter of 25 μm was mixed with a (meth)acrylate compound used in the present invention so as to be a concentration of 20% by weight, and the mixture was then stirred. After 5 hours, evaluation was made in accordance with the following evaluation criterion by observing the state of each mixture.

Evaluation Criterion
S. . . soluble
SW. . . swelled
IS. . . insoluble

TABLE 1

| | Compound | Odor Test | Irri- tation Test | Polymer Solubility Test |
|---|---|---|---|---|
| Example 1 | A | ○-△ | △ | S |
| Example 2 | B | ○-△ | ○ | S |
| Example 3 | C | ○ | ○ | S |
| Example 4 | D | ○ | ○ | SW |
| Example 5 | E | △ | ○ | S |
| Example 6 | F | ○-△ | △ | S |
| Example 7 | G | ○ | ○ | SW |
| Example 8 | H | ○ | ○ | SW |
| Comp. Ex. 1 | methyl methacrylate | X | X | S |
| Comp. Ex. 2 | ethyl methacrylate | X | X | S |
| Comp. Ex. 3 | iso-propyl methacrylate | X | X | SW |
| Comp. Ex. 4 | iso-butyl methacrylate | X | △ | SW |

EXAMPLES 9 TO 19

The same procedure as in Example 2 was effected except that mixtures of monomers were used as test compounds. The results are set forth in Table 2.

TABLE 2 (I)

| | Mixture of Monomers | |
|---|---|---|
| | I | II |
| Example 9 | Compound B | cyclohexyl methacrylate |
| Example 10 | " | lauryl methacrylate |
| Example 11 | " | tridecyl methacrylate |
| Example 12 | " | ethylene glycol dimethacrylate |
| Example 13 | " | triethylene glycol dimethacrylate |
| Example 14 | " | 1,6-hexanediol dimethacrylate |
| Example 15 | " | 2,2-bis(4-methacryloyloxyethoxyphenyl)propane |
| Example 16 | " | neopentyl glycol dimethacrylate |
| Example 17 | " | trimethylolpropane trimethacrylate |
| Example 18 | " | 1,6-hexanediol dimethacrylate |
| Example 19 | " | 1,6-hexanediol dimethacrylate |

TABLE 2 (II)

| | Mixing Weight Ratio (I/II) | Odor Test | Irri- tation Test | Polymer Solubility Test |
|---|---|---|---|---|
| Example 9 | 70/30 | △ | ○ | S |
| Example 10 | " | ○ | ○ | S |
| Example 11 | " | ○ | ○ | S |
| Example 12 | " | ○ | ○ | S |
| Example 13 | " | ○ | ○ | S |
| Example 14 | " | ○ | ○ | S |
| Example 15 | " | ○ | ○ | S |
| Example 16 | " | ○ | ○ | S |
| Example 17 | " | ○ | ○ | S |
| Example 18 | 50/50 | ○ | ○ | S |
| Example 19 | 40/60 | ○ | ○ | S |

EXAMPLES 20 TO 26, COMPARATIVE EXAMPLES 5 AND 6

In each monomer solution shown in Table 3 was dissolved 0.5% by weight (with respect to the monomer solution) of benzoyl peroxide, and the solution was then placed in a glass tube and the latter was sealed up. Afterward, the glass tube was heated at 60° C. for 24 hours, and successively it was further heated at 100° C. for 24 hours in order to carry out polymerization, thereby obtaining a cured product. Next, for each cured product, performance was evaluated by the following procedure, and the results are set forth in Table 3.

Performance Evaluation of Cured Product

Indirect Tensile (Diametral) Strength

Each test piece was molded into the form of a 6×6 mm$\phi$ cylinder. An indirect tensile test was employed in which there was utilized the phenomenon that tensile stress was produced at right angles to compressive force by applying the compressive force in a diameter direction of the cylindrical test piece. The tensile strength was calculated in accordance with the following formula:

$$\text{Tensile strength} = (2 \times C)/(\pi \times D \times L)$$

C = compression load,
D = diameter of the test piece, and
L = length of the test piece.

Amount of Absorbed Water

Each test piece was molded into the form of a 10×1 mm$\phi$ cylinder. The test piece was immersed in water at 37° C. for 7 days, and an amount of absorbed water per unit area of the test piece was then measured.

TABLE 3

| | Monomer Solution | Indirect Tensile Strength (kgf/cm$^2$) | Amount of Absorbed Water (mg/cm$^2$) |
|---|---|---|---|
| Example 20 | Compound B | 275 | 0.51 |
| Example 21 | Compound D | 230 | 0.45 |
| Example 22 | Compound F | 262 | 0.50 |
| Example 23 | Compound A/Compound B = 30/70 (weight ratio) | 280 | 0.55 |
| Example 24 | Compound A/Compound B = 70/30 | 288 | 0.57 |
| Example 25 | Compound B/1,6-hexanediol dimethacrylate = 50/50 | 375 | 0.58 |

TABLE 3-continued

|  | Monomer Solution | Indirect Tensile Strength (kgf/cm$^2$) | Amount of Absorbed Water (mg/cm$^2$) |
|---|---|---|---|
| Example 26 | Compound B/trimethylolpropane trimethacrylate = 50/50 | 408 | 0.58 |
| Comp. Ex. 5 | butyl methacrylate | 188 | 0.98 |
| Comp. Ex. 6 | CH$_3$<br>CH$_2$=C—COOC$_2$H$_4$OCOCH$_2$CH$_3$ | 270 | 1.02 |

EXAMPLES 27 TO 37

Each polymer powder shown in Table 4 was mixed with a monomer solution at a weight ratio of 30/70 in which 0.5% by weight (with respect to the monomer solution) of benzoyl peroxide was dissolved, and the mixture was then placed in a glass tube. The latter was then sealed up and heated at 60° C. for 24 hours and successively heated at 100° C. for 24 hours in order to carry out polymerization, thereby obtaining a cured product. Next, for the thus cured product, performance was evaluated by the same procedure as in Example 20. The results are set forth in Table 4.

TABLE 4

| | Composition of Powder-Solution Mixture | | Indirect Tensile Strength (kgf/cm$^2$) | Amount of Absorbed Water (mg/cm$^2$) |
|---|---|---|---|---|
| | Polymer Powder | Monomer Solution | | |
| Example 27 | PMMA (*1) | Compound A | 301 | 0.59 |
| Example 28 | PEMA (*2) | " | 270 | 0.55 |
| Example 29 | methyl methacrylate/ethyl methacrylate copolymer (*3) | " | 285 | 0.57 |
| Example 30 | methyl methacrylate/butyl methacrylate copolymer (*4) | " | 265 | 0.58 |
| Example 31 | polystyrene (*5) | " | 286 | 0.52 |
| Example 32 | polybutyl methacrylate [PBMA] (*6) | " | 250 | 0.56 |
| Example 33 | methyl methacrylate/styrene copolymer (*7) | " | 295 | 0.57 |
| Example 34 | ethyl methacrylate/butyl methacrylate copolymer (*8) | " | 255 | 0.56 |
| Example 35 | ethyl methacrylate/styrene copolymer (*9) | " | 280 | 0.54 |
| Example 36 | PMMA/PEMA = 50/50 (weight ratio) | " | 279 | 0.57 |
| Example 37 | PEMA/PBMA = 50/50 (weight ratio) | " | 242 | 0.56 |

Properties of Polymers

The abbreviations, MW, PS and CP mean an average molecular weight, an average particle diameter and a composition of each copolymer, respectively.

(*1) MW: 480×10$^3$, PS: 15 μm
(*2) MW: 230×10$^3$, PS: 25 μm
(*3) CP: 40/60, MW: 320×10$^3$, PS: 20 μm
(*4) CP: 40/60, MW: 60×10$^3$, PS: 23 μm
(*5) MW: 120×10$^3$, PS: 30 μm
(*6) MW: 360×10$^3$, PS: 42 μm
(*7) CP: 75/25, MW: 85×10$^3$, PS: 84 μm
(*8) CP: 50/50, MW: 780×10$^3$, PS: 12 μm
(*9) CP: 50/50, MW: 520×10$^3$, PS: 18 μm

EXAMPLES 38 TO 40

Each PEMA powder having an average particle diameter shown in Table 5 (average molecular weight=230×10$^3$) was mixed with a monomer mixture comprising compound B/1,6-hexanediol dimethacrylate=36/64 (weight ratio) at a weight ratio of 2:1, and for the resulting mixture, a period for dough stage was then measured by the following test procedure. The results are set forth in Table 5.

Test Procedure of Period for Dough Stage

Predetermined amounts of a polymer powder and a monomer solution are weighed in a weighing bottle (inner diameter 47 mm, height 2 cm), and after stirring for 20 seconds, the weighing bottle is covered with a lid of reinforced glass, followed by allowing the bottle to stand for 5 minutes. After stirring for 20 seconds again, the weighing bottle is covered with the reinforced glass lid and then allowed to stand for 5 minutes. The starting point of the period for dough stage is when it has been confirmed by touching the surface of the sample with a finger that the sample is not tacky any more. The sample is then separated from the wall surface of the weighing bottle by moving a metallic needle along the inside wall of the bottle. The end point of the period for dough stage is when the sample is inverted by piercing the stem of a spoon into the sample. A pot life is obtained from the formula of (the end point of the period for dough stage)—(the starting point of the period for dough stage).

TABLE 5

| | Average Diameter of PEMA Powder (μm) | Period for Dough Stage (min) | | |
|---|---|---|---|---|
| | | End | Start | Pot Life |
| Example 38 | 95 | 77 | 24 | 53 |
| Example 39 | 84 | 69 | 22 | 47 |
| Example 40 | 78 | 46 | 20 | 26 |

SYNTHESIS EXAMPLE 1

(synthesis of $H_2C=\overset{CH_3}{\underset{|}{C}}-\underset{\underset{O}{\|}}{C}O-(CH_2)_2-\underset{\underset{O}{\|}}{C}-CH_3$)

In a 500-milliliter four-necked flask equipped with a condenser tube, a nitrogen-introducing pipe, a stirring rod and a thermocouple were placed 1 mole of methacrylic acid as an unsaturated carboxylic acid, 0.8 mole of thionyl chloride, a small amount of hydroquinone and 10 drops of DMF (dimethylformamide) as a catalyst, and they were then mixed and reacted for 15 hours in a water bath. Afterward, 0.8 mole of 4-hydroxy-2-butanone(γ-ketobutanol) was added to the reaction solution, and reaction was then carried out at a temperature of from 40° to 50° C. for 3 hours. The reaction solution was dispersed in an excessive amount of water, and the resulting dispersion was then extracted with 400 ml of methylene chloride and the extract (the methylene chloride solution) was separated, washed with 300 ml of water twice, neutralized with sodium bicarbonate, washed, and acidified with hydrochloric acid. Anhydrous magnesium sulfate was added to the methylene chloride solution, and the solution was then dehydrated, followed by filtration. The solvent in the filtrate was vaporized under reduced pressure by the use of an aspirator, and finally the solvent was removed therefrom at 50° C. for 30 minutes, so that the desired specific methacrylate compound was obtained.

Figure 1:
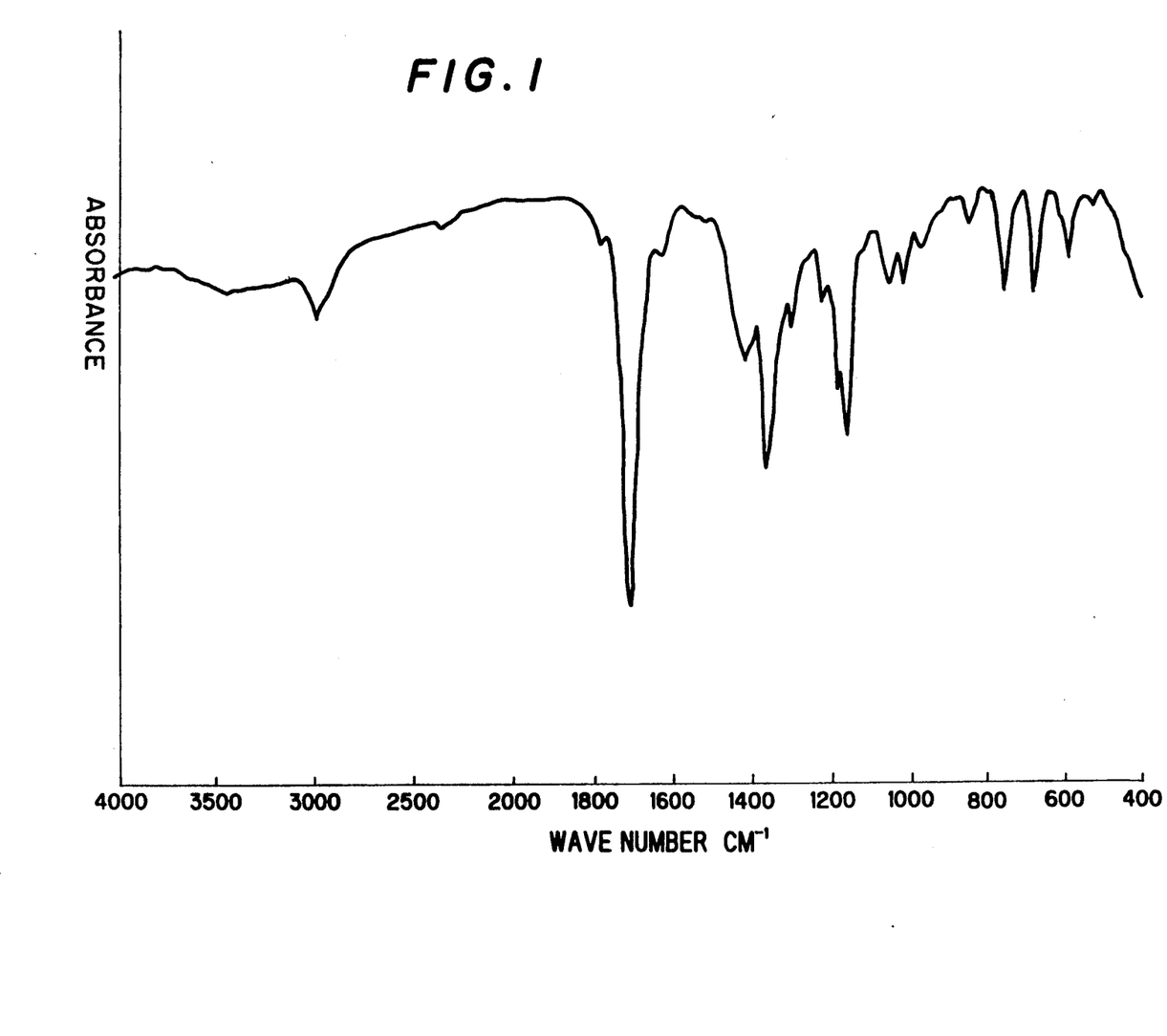
FIG. 1 is an IR chart of a methacrylate obtained in Synthesis Example 1.

In this case, the yield of the thus obtained compound was about 50 g. The IR chart of this compound is shown in FIG. 1. Other compounds represented by the general formula (2) could be synthesized by the same procedure as described above.

EXAMPLES 41 TO 45

The following compounds were used as specific (meth)acrylate compounds represented by the general formula (2) according to the present invention, and an odor test, an irritation test and a polymer solubility test were carried out in the same procedure as in Example 1.

Compound I $H_2C=\overset{CH_3}{\underset{|}{C}}-\underset{\underset{O}{\|}}{C}O-(CH_2)_2-\underset{\underset{O}{\|}}{C}-CH_3$ Compound J $H_2C=\overset{CH_3}{\underset{|}{C}}-\underset{\underset{O}{\|}}{C}O-(CH_2)_2-\underset{\underset{O}{\|}}{C}-CH_2CH_3$ Compound K $H_2C=\overset{CH_3}{\underset{|}{C}}-\underset{\underset{O}{\|}}{C}O-(CH_2)_4-\underset{\underset{O}{\|}}{C}-CH_2CH_3$ Compound L $H_2C=\overset{CH_3}{\underset{|}{C}}-\underset{\underset{O}{\|}}{C}O-(CH_2)_6-\underset{\underset{O}{\|}}{C}-CH_2CH_3$ Compound M $H_2C=\overset{CH_3}{\underset{|}{C}}-\underset{\underset{O}{\|}}{C}O-(CH_2)_4-\underset{\underset{O}{\|}}{C}-(CH_2)_3-CH_3$ The results are set forth in Table 6.

TABLE 6

| | Compound | Odor Test | Irritation Test | Polymer Solubility Test |
|---|---|---|---|---|
| Example 41 | I | ○-△ | ○-△ | S |
| Example 42 | J | ○-△ | ○ | S |
| Example 43 | K | ○ | ○ | S |
| Example 44 | L | ○ | ○ | S |
| Example 45 | M | ○ | ○ | S |
| Comp. Ex. 1 | methyl methacrylate | X | X | S |
| Comp. Ex. 2 | ethyl methacrylate | X | X | S |
| Comp. Ex. 4 | isobutyl methacrylate | X | △ | SW |

EXAMPLES 46 TO 56

The same procedure as in Example 43 was effected except that compounds for tests were mixtures of monomers, and the results are set forth in Table 7.

TABLE 7 (I)

| | Mixture of Monomers | |
|---|---|---|
| | I | II |
| Example 46 | Compound K | cyclohexyl methacrylate |
| Example 47 | " | lauryl methacrylate |
| Example 48 | " | tridecyl methacrylate |
| Example 49 | " | ethylene glycol dimethacrylate |
| Example 50 | " | triethylene glycol dimethacrylate |
| Example 51 | " | 1,6-hexanediol dimethacrylate |
| Example 52 | " | neopentyl glycol dimethacrylate |
| Example 53 | " | 2,2-bis(4-methacryloxy-phenyl)propane |
| Example 54 | " | trimethylolpropane trimethacrylate |
| Example 55 | " | 1,6-hexanediol dimethacrylate |
| Example 56 | " | 1,6-hexanediol dimethacrylate |

TABLE 7 (II)

| | Mixing Weight Ratio (I/II) | Odor Test | Irritation Test | Polymer Solubility Test |
|---|---|---|---|---|
| Example 46 | 70/30 | ○-△ | ○ | S |
| Example 47 | " | ○ | ○ | S |
| Example 48 | " | ○ | ○ | S |
| Example 49 | " | ○ | ○ | S |
| Example 50 | " | ○ | ○ | S |
| Example 51 | " | ○ | ○ | S |
| Example 52 | " | ○ | ○ | S |
| Example 53 | " | ○ | ○ | S |
| Example 54 | " | ○ | ○ | S |

TABLE 7 (II)-continued

| | Mixing Weight Ratio (I/II) | Odor Test | Irritation Test | Polymer Solubility Test |
|---|---|---|---|---|
| Example 55 | 50/50 | ○ | ○ | S |
| Example 56 | 40/60 | ○ | ○ | S |

EXAMPLES 57 TO 62

In each monomer solution shown in Table 8 was dissolved 0.5% by weight (with respect to the monomer solution) of benzoyl peroxide, and the solution was then placed in a glass tube and the latter was sealed up. Afterward, the glass tube was heated at 60° C. for 24 hours, and successively it was further heated at 100° C. for 24 hours in order to carry out polymerization, thereby obtaining a cured product. Next, for each cured product, performance was evaluated by the same procedure as in Example 20, and the results are set forth in Table 8.

TABLE 8

| | Monomer Solution | Indirect Tensile Strength (kgf/cm$^2$) | Amount of Absorbed Water (mg/cm$^2$) |
|---|---|---|---|
| Example 57 | Compound J | 248 | 0.52 |
| Example 58 | Compound K | 260 | 0.48 |
| Example 59 | Compound M | 256 | 0.49 |
| Example 60 | Compound J/Compound K = 30/70 (weight ratio) | 267 | 0.58 |
| Example 61 | Compound J/Compound K = 70/30 (weight ratio) | 252 | 0.57 |
| Example 62 | Compound K/1,6-hexanediol dimethacrylate = 50/50 (weight ratio) | 348 | 0.58 |
| Comp. Ex. 5 | isobutyl methacrylate | 188 | 0.98 |
| Comp. Ex. 6 | $CH_2=\overset{CH_3}{\underset{|}{C}}-COO-C_2H_4OCOC_2H_5$ | 270 | 1.02 |

EXAMPLES 63 TO 73

Each polymer powder shown in Table 9 was mixed with a monomer solution at a weight ratio of 30/70 in which 0.5% by weight (with respect to the monomer solution) of benzoyl peroxide was dissolved, and the mixture was then placed in a glass tube. The latter was then sealed up and heated at 60° C. for 24 hours and successively heated at 100° C. for 24 hours in order to carry out polymerization, thereby obtaining a cured product. Next, for the thus cured product, performance was evaluated by the same procedure as in Example 58. The results are set forth in Table 9.

In this connection, properties of the polymer powders used in these examples were the same as in Examples 27 to 37.

TABLE 9

| | Composition of Powder-Solution Mixture | | Indirect Tensile Strength (kgf/cm$^2$) | Amount of Absorbed Water (mg/cm$^2$) |
|---|---|---|---|---|
| | Polymer Powder | Monomer Solution | | |
| Example 63 | PMMA (*1) | Compound K | 250 | 0.57 |
| Example 64 | PEMA (*2) | " | 270 | 0.57 |
| Example 65 | methyl methacrylate/ethyl methacrylate copolymer (*3) | " | 276 | 0.60 |
| Example 66 | methyl methacrylate/butyl methacrylate copolymer (*4) | " | 261 | 0.55 |
| Example 67 | polystyrene (*5) | " | 244 | 0.58 |
| Example 68 | polybutyl methacrylate [PBMA] (*6) | " | 268 | 0.63 |
| Example 69 | methyl methacrylate/styrene copolymer (*7) | " | 250 | 0.60 |
| Example 70 | ethyl methacrylate/butyl methacrylate copolymer (*8) | " | 239 | 0.59 |
| Example 71 | ethyl methacrylate/styrene copolymer (*9) | " | 235 | 0.53 |
| Example 72 | PMMA/PEMA = 50/50 (weight ratio) | " | 252 | 0.59 |
| Example 73 | PEMA/PBMA = 50/50 (weight ratio) | " | 238 | 0.57 |

EXAMPLES 74 TO 76

Each PEMA powder having an average particle diameter shown in Table 10 (average molecular weight=230×10$^3$) was mixed with a monomer mixture comprising Compound J/1,6-hexanediol dimethacrylate=36/64 (weight ratio) at a ratio of 2:1, and for the resulting mixture, a dough stage time was then measured by the same procedure as in Example 38. The results are set forth in Table 10.

TABLE 10

| | Average Diameter of PEMA Powder (μm) | Dough Stage Time (min) | | |
|---|---|---|---|---|
| | | End | Start | Pot Life |
| Example 74 | 84 | 64 | 13 | 51 |
| Example 75 | 52 | 45 | 15 | 30 |
| Example 76 | 25 | 31 | 16 | 15 |

SYNTHESIS EXAMPLE 2

(synthesis of )

Figure 2:
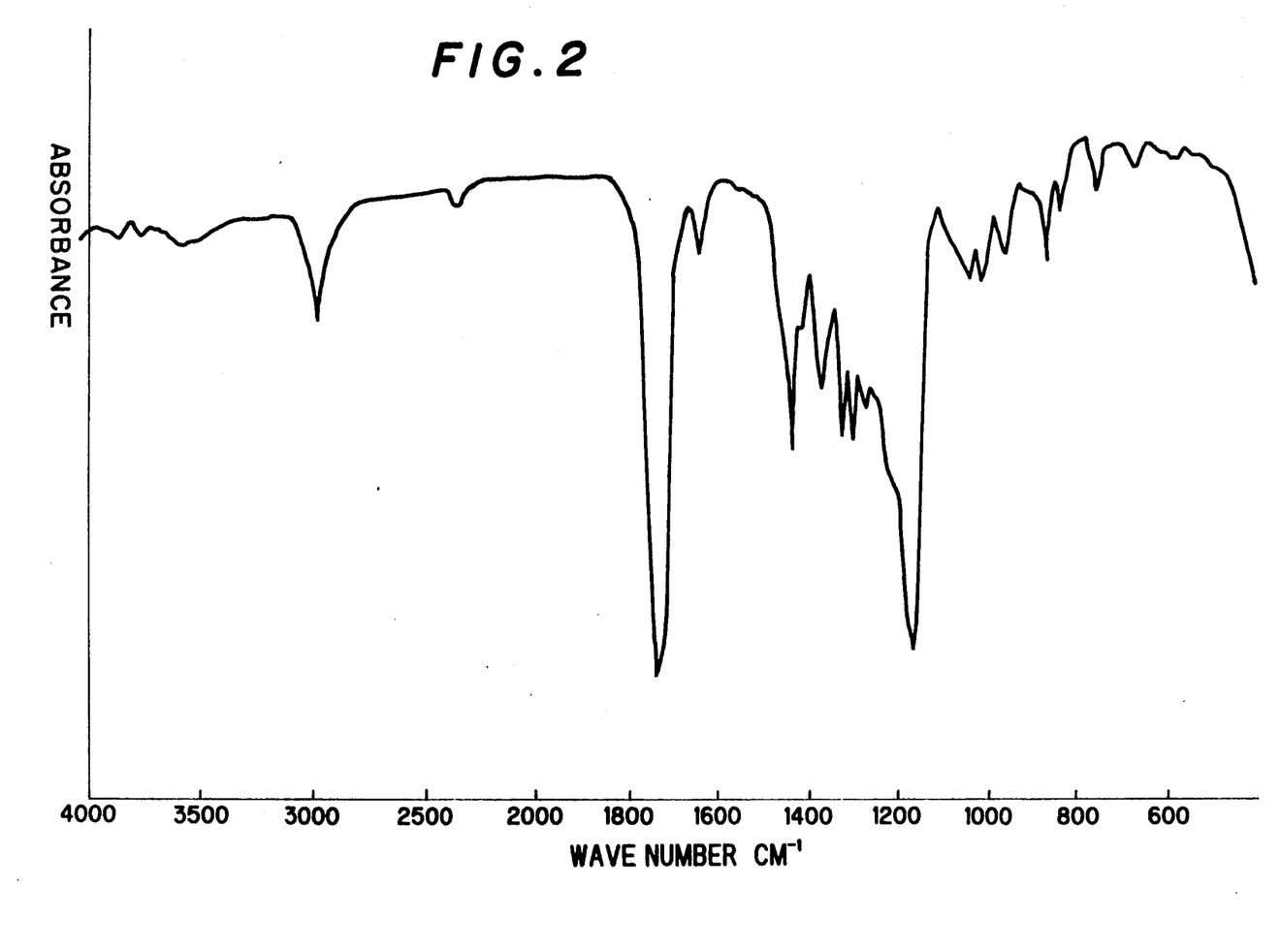
FIG. 2 is an IR chart of a methacrylate obtained in Synthesis Example 2.

In a 2,000-milliliter four-necked flask equipped with a cooling pipe, a nitrogen-introducing pipe, a stirring rod and a thermocouple was placed 115 g of the acrylic ester SA [$CH_2=C(CH_3)COOC_2H_4OCOC_2H_4COOH$] made by Mitsubishi Rayon Co., Ltd. as an unsaturated carboxylic acid, 500 ml of methanol, 2.5 g of concentrated hydrochloric acid and a small amount of hydroquinone, and they are mixed, Afterward, the mixture was allowed to stand at room temperature (abut 20° C.) for 3 days. Next, 500 ml of water was added to the mixture to dilute it and then extracted with 200 ml of methylene chloride twice, and the extract was washed with 300 ml of water twice and with an aqueous saturated sodium hydrogen carbonate solution once, and dried over anhydrous magnesium sulfate, followed by filtration. The solution was concentrated under reduced pressure by the use of an aspirator, and finally, the solvent was distilled off at 50° C for 30 minutes, so that the desired specific methacrylate compound was obtained. In this case, the yield of the thus obtained compound was about 100.1 g. The IR chart of this product is shown in FIG. 2.

Other compounds represented by the general formula (3) could be synthesized in accordance with the similar reaction by the use of a suitable unsaturated carboxylic acid and an alcohol.

EXAMPLES 77 TO 81

The following compounds were used as typical (meth)acrylate compounds represented by the general formula (3) according to the present invention, and an odor test, an irritation test and a polymer solubility test were carried out in the same procedure as in Example 1.

Compound N

Compound P

Compound Q

Compound R

Compound S

TABLE 11

| | Compound | Odor Test | Irritation Test | Polymer Solubility Test |
|---|---|---|---|---|
| Example 77 | N | ○-△ | ○-△ | S |
| Example 78 | P | ○ | ○ | S |
| Example 79 | Q | ○ | ○ | SW |
| Example 80 | R | ○ | ○ | S |
| Example 81 | S | ○ | ○ | SW |
| Comp. Ex. 1 | methyl methacrylate | X | X | S |
| Comp. Ex. 2 | ethyl methacrylate | X | X | S |
| Comp. Ex. 4 | isobutyl methacrylate | X | △ | SW |

EXAMPLES 82 TO 92

The same procedure as in Example 78 was effected except that compounds for tests were mixtures of monomers, and the results are set forth in Table 12.

TABLE 12 (I)

| | Mixture of Monomers | |
|---|---|---|
| Example 82 | Compound P | cyclohexyl methacrylate |
| Example 83 | " | lauryl methacrylate |
| Example 84 | " | tridecyl methacrylate |
| Example 85 | " | ethylene glycol dimethacrylate |
| Example 86 | " | triethylene glycol dimethacrylate |
| Example 87 | " | 1,6-hexanediol dimethacrylate |
| Example 88 | " | neopentyl glycol dimethacrylate |
| Example 89 | " | 2,2-bis(4-methacryloyloxyethoxyphenyl)propane |
| Example 90 | " | trimethylolpropane trimethacrylate |
| Example 91 | " | 1,6-hexanediol dimethacrylate |
| Example 92 | " | 1,6-hexanediol dimethacrylate |

TABLE 12 (II)

| | Mixing Weight Ratio (I/II) | Odor Test | Irritation Test | Polymer Solubility Test |
|---|---|---|---|---|
| Example 82 | 70/30 | ○-△ | ○ | S |
| Example 83 | " | ○ | ○ | S | dure as in Example 20, and the results are set forth in Table 13.

TABLE 13

| | Monomer Solution | Indirect Tensile Strength (kgf/cm$^2$) | Amount of Absorbed Water (mg/cm$^2$) |
|---|---|---|---|
| Example 93 | Compound N | 260 | 0.73 |
| Example 94 | Compound P | 278 | 0.69 |
| Example 95 | Compound S | 254 | 0.62 |
| Example 96 | Compound N/Compound P = 30/70 (weight ratio) | 281 | 0.68 |
| Example 97 | Compound N/Compound P = 70/30 (weight ratio) | 275 | 0.67 |
| Example 98 | Compound P/1,6-hexane-diol dimethacrylate = 50/50 (weight ratio) | 345 | 0.75 |
| Comp. Ex. 5 | isobutyl methacrylate | 188 | 0.98 |
| Comp. Ex. 6 | $CH_2\!=\!\underset{\underset{\displaystyle CH_3}{\vert}}{C}\!-\!COO\!-\!C_2H_4OCOC_2H_5$ | 270 | 1.02 |

TABLE 12 (II)-continued

| | Mixing Weight Ratio (I/II) | Odor Test | Irritation Test | Polymer Solubility Test |
|---|---|---|---|---|
| Example 84 | " | ○ | ○ | S |
| Example 85 | " | ○ | ○ | S |
| Example 86 | " | ○ | ○ | S |
| Example 87 | " | ○ | ○ | S |
| Example 88 | " | ○ | ○ | S |
| Example 89 | " | ○ | ○ | S |
| Example 90 | " | ○ | ○ | S |
| Example 91 | 50/50 | ○ | ○ | S |
| Example 92 | 40/60 | ○ | ○ | S |

EXAMPLES 93 TO 98

In each monomer solution shown in Table 13 was dissolved 0.5% by weight (with respect to the monomer solution) of benzoyl peroxide, and the solution was then placed in a glass tube and the latter was sealed up. Afterward, the glass tube was heated at 60° C. for 24 hours, and successively it was further heated at 100° C. for 24 hours in order to carry out polymerization, thereby obtaining a cured product. Next, for each cured product, performance was evaluated by the same procedure as in Example 20, and the results are set forth in Table 13.

EXAMPLES 99 TO 109

Each polymer powder shown in Table 14 was mixed with a monomer solution at a weight ratio of 30/70 in which 0.5% by weight (with respect to the monomer solution) of benzoyl peroxide was dissolved, and the mixture was then placed in a glass tube. The latter was then sealed up and heated at 60° C. for 24 hours and successively heated at 100° C. for 24 hours in order to carry out polymerization, thereby obtaining a cured product. Next, for the thus cured product, performance was evaluated by the same procedure as in Example 94. The results are set forth in Table 14.

In this connection, properties of the polymer powders used in these examples were the same as in Examples 27 to 37.

TABLE 14

| | Composition of Powder-Solution Mixture | | Indirect Tensile Strength (kgf/cm$^2$) | Amount of Absorbed Water (mg/cm$^2$) |
|---|---|---|---|---|
| | Polymer Powder | Monomer Solution | | |
| Example 99 | PMMA (*1) | Compound P | 264 | 0.68 |
| Example 100 | PEMA (*2) | " | 299 | 0.66 |
| Example 101 | methyl methacrylate/ ethyl methacrylate copolymer (*3) | " | 304 | 0.71 |
| Example 102 | methyl methacrylate/ butyl methacrylate copolymer (*4) | " | 270 | 0.65 |
| Example 103 | polystyrene (*5) | " | 258 | 0.70 |
| Example 104 | polybutyl methacrylate (PBMA) (*6) | " | 286 | 0.75 |
| Example 105 | methyl methacrylate/ styrene copolymer (*7) | " | 267 | 0.69 |
| Example 106 | ethyl methacrylate/ butyl methacrylate copolymer (*8) | " | 280 | 0.68 |
| Example 107 | ethyl methacrylate/ styrene copolymer (*9) | " | 261 | 0.62 |
| Example 108 | PMMA/PEMA = 50/50 (weight ratio) | " | 260 | 0.68 |
| Example 109 | PEMA/PBMA = 50/50 (weight ratio) | " | 268 | 0.66 |

EXAMPLES 110 TO 112

Each PEMA powder having an average particle diameter shown in Table 15 (average molecular weight = 230 × 10$^3$) was mixed with a monomer mixture comprising Compound P/1,6-hexanediol dimethacrylate = 36/64 (weight ratio) at a ratio of 2:1, and for the resulting mixture, a period for dough stage was then measured by the same procedure as in Example 38. The results are set forth in Table 15.

TABLE 15

| | Average Diameter of PEMA Powder (μm) | Period for Dough Stage (min) | | |
|---|---|---|---|---|
| | | End | Start | Pot Life |
| Example 110 | 84 | 75 | 22 | 53 |
| Example 111 | 52 | 49 | 19 | 30 |
| Example 112 | 25 | 36 | 18 | 18 |

SYNTHESIS EXAMPLE 3

[synthesis of $H_2C=C-CH_2CH_2CH-C-O-CH_3$ (D-MMA)]

In a 1-liter stainless steel autoclave were placed 400 g of methyl methacrylate and 2 g of hydroquinone. Next, the atmosphere in the reactor was replaced with an $N_2$ gas several times, and the reactor was then sealed up. Afterward, the reactor was heated at 225° C. for 12 hours to carry out a thermal dimerization reaction.

The component having a boiling point of 107° C. (7 mmHg) in the reaction product was fractionated, and as a result, 90.5 g of a colorless and transparent liquid was obtained. Properties of this component were as follows:

specific gravity: 1.0397 g/cm$^3$ (25° C.)
$\eta^{25}_D$: 1.4488
$\eta$: 4.09 cp (25° C.)

Figure 3:
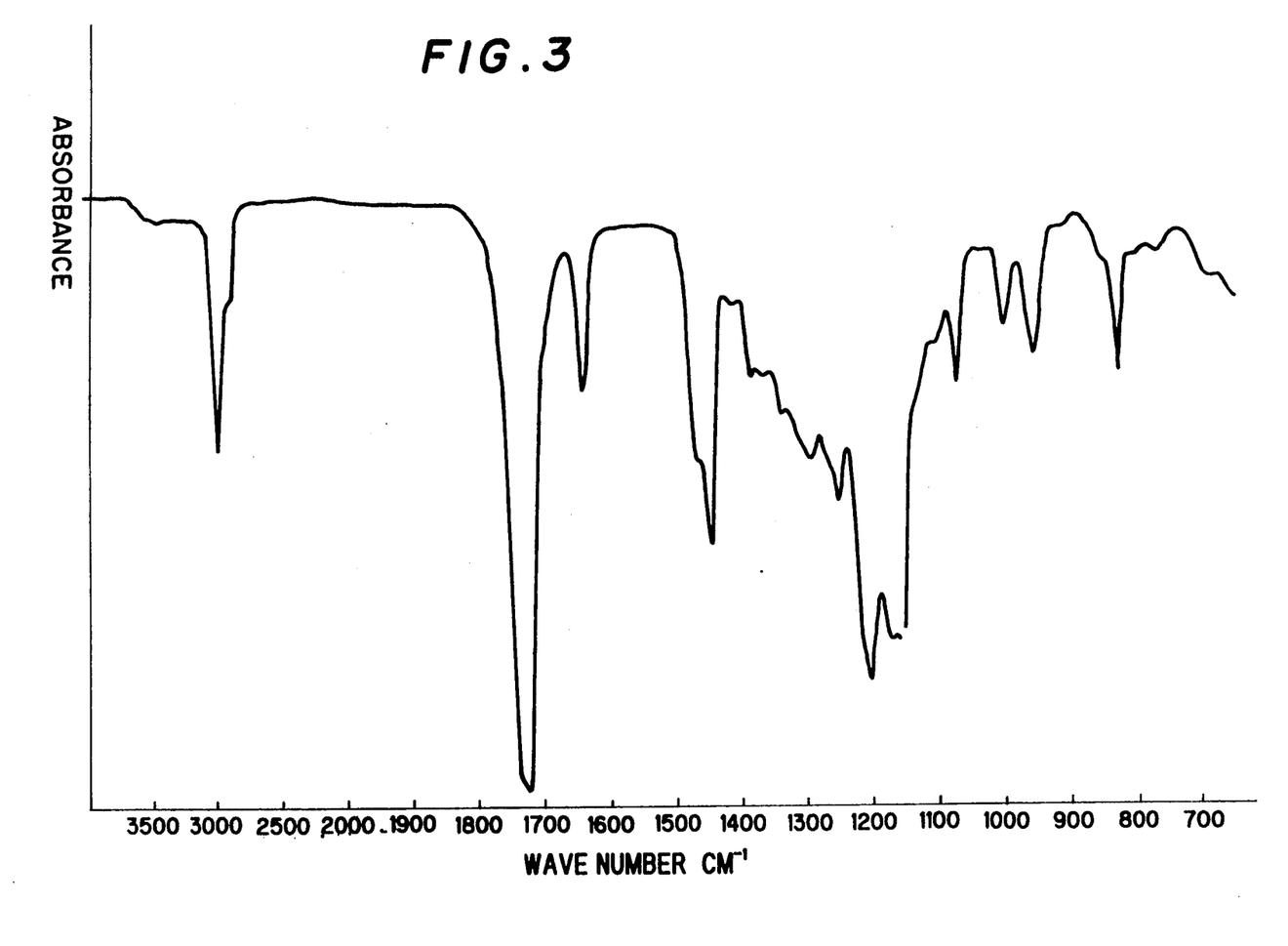
FIG. 3 is an IR chart of D-MMA obtained in Synthesis Example 3.

It was confirmed from a literature [J. Am. Chem. Soc., 78, 472 (1956)] that the above component was the desired D-MMA. The infrared absorption spectrum of the desired product is shown in FIG. 3.

EXAMPLE 113

A specific methacrylate dimer (D-MMA) of the present invention was used, and an odor test, an irritation test and a polymer solubility test were carried out in the same procedure as in Example 1.

The results are set forth in Table 16.

TABLE 16

| | Compound | Odor Test | Irritation Test | Polymer Solubility Test |
|---|---|---|---|---|
| Example 113 | D-MMA | ○-△ | ○-△ | S |
| Comp. Ex. 1 | methyl methacrylate | X | X | S |
| Comp. Ex. 2 | ethyl methacrylate | X | X | S |
| Comp. Ex. 4 | isobutyl methacrylate | X | △ | SW |

EXAMPLES 114 TO 124

The same procedure as in Example 113 was effected except that compounds for tests were mixtures of monomers, and the results are set forth in Table 17.

TABLE 17 (I)

| | Mixture of Monomers | |
|---|---|---|
| Example 114 | Compound D-MMA | cyclohexyl methacrylate |
| Example 115 | " | lauryl methacrylate |
| Example 116 | " | tridecyl methacrylate |
| Example 117 | " | ethylene glycol dimethacrylate |
| Example 118 | " | triethylene glycol dimethacrylate |
| Example 119 | " | 1,6-hexanediol dimethacrylate |
| Example 120 | " | neopentyl glycol dimethacrylate |
| Example 121 | " | 2,2-bis(4-methacryloxyethoxyphenyl)propane |
| Example 122 | " | trimethylolpropane trimethacrylate |
| Example 123 | " | 1,6-hexanediol dimethacrylate |
| Example 124 | " | 1,6-hexanediol dimethacrylate |

TABLE 17 (II)

| | Mixing Weight Ratio (I/II) | Odor Test | Stimulation Test | Polymer Solubility Test |
|---|---|---|---|---|
| Example 114 | 70/30 | ○-△ | ○ | S |
| Example 115 | " | ○ | ○ | S |
| Example 116 | " | ○ | ○ | S |
| Example 117 | " | ○ | ○ | S |
| Example 118 | " | ○ | ○ | S |
| Example 119 | " | ○ | ○ | S |
| Example 120 | " | ○ | ○ | S |
| Example 121 | " | ○ | ○ | S |
| Example 122 | " | ○ | ○ | S |
| Example 123 | 50/50 | ○ | ○ | S |
| Example 124 | 40/60 | ○ | ○ | S |

EXAMPLES 125 TO 126

In each monomer solution shown in Table 18 was dissolved 0.5% by weight (with respect to the monomer solution) of benzoyl peroxide, and the solution was then placed in a glass tube and the latter was sealed up. Afterward, the glass tube was heated at 60° C. for 24 hours, and successively it was further heated at 100° C. for 24 hours in order to carry out polymerization, thereby obtaining a cured product. Next, for each cured product, performance was evaluated by the same procedure as in Example 20, and the results are set forth in Table 18.

TABLE 18

| | Monomer Solution | Indirect Tensile Strength (kgf/cm$^2$) | Amount of Absorbed Water (mg/cm$^2$) |
|---|---|---|---|
| Example 125 | D-MMA | 250 | 0.55 |
| Example 126 | D-MMA/1,6-hexanediol dimethacrylate 50/50 | 350 | 0.59 |
| Comp. Ex. 5 | isobutyl methacrylate | 188 | 0.98 |

TABLE 18-continued

|  | Monomer Solution | Indirect Tensile Strength (kgf/cm$^2$) | Amount of Absorbed Water (mg/cm$^2$) |
|---|---|---|---|
| Comp. Ex. 6 | $\text{CH}_2=\overset{\overset{\text{CH}_3}{\mid}}{\text{C}}-\text{COO}-\text{C}_2\text{H}_4\text{OCOC}_2\text{H}_5$ | 270 | 1.02 |

EXAMPLES 127 TO 137

Each polymer powder shown in Table 19 was mixed with a monomer solution at a weight ratio of 30/70 in which 0.5% by weight (with respect to the monomer solution) of benzoyl peroxide was dissolved, and the mixture was then placed in a glass tube. The latter was then sealed up and heated at 60° C. for 24 hours and successively heated at 100° C. for 24 hours in order to carry out polymerization, thereby obtaining a cured product. Next, for the thus cured product, performance was evaluated by the same procedure as in Example 125. The results are set forth in Table 19.

In this connection, properties of the polymer powders 5 used in these examples were the same as in Examples 27 to 37.

TABLE 19

|  | Composition of Powder-Solution Mixture | | Indirect Tensile Strength (kgf/cm$^2$) | Amount of Absorbed Water (mg/cm$^2$) |
|---|---|---|---|---|
|  | Polymer Powder | Monomer Solution | | |
| Example 127 | PMMA (*1) | D-MMA | 252 | 0.60 |
| Example 128 | PEMA (*2) | " | 272 | 0.60 |
| Example 129 | methyl methacrylate/ ethyl methacrylate copolymer (*3) | " | 278 | 0.65 |
| Example 130 | methyl methacrylate/ butyl methacrylate copolymer (*4) | " | 263 | 0.58 |
| Example 131 | polystyrene (*5) | " | 246 | 0.61 |
| Example 132 | polybutyl methacrylate (PBMA) (*6) | " | 270 | 0.66 |
| Example 133 | methyl methacrylate/ styrene copolymer (*7) | " | 252 | 0.63 |
| Example 134 | ethyl methacrylate/ butyl methacrylate copolymer (*8) | " | 241 | 0.62 |
| Example 135 | ethyl methacrylate/ styrene copolymer (*9) | " | 237 | 0.58 |
| Example 136 | PMMA/PEMA = 50/50 (weight ratio) | " | 254 | 0.61 |
| Example 137 | PEMA/PBMA = 50/50 (weight ratio) | " | 240 | 0.60 |

EXAMPLES 137 TO 140

Each PEMA powder having an average particle diameter shown in Table 20 (average molecular weight=230×10$^3$) was mixed with a monomer mixture comprising D-MMA/1,6-hexanediol dimethacrylate=36/64 (weight ratio) at a ratio of 2:1, and for the resulting mixture, a dough stage time was then measured by the same procedure as in Example 38. The results are set forth in Table 20.

TABLE 20

|  | Average Diameter of PEMA Powder (μm) | Period for Dough Stage (min) | | |
|---|---|---|---|---|
|  |  | End | Start | Pot Life |
| Example 138 | 84 | 62 | 12 | 50 |
| Example 139 | 52 | 42 | 17 | 25 |
| Example 140 | 25 | 30 | 15 | 15 |

What is claimed is:

1. A material for dentistry which is prepared by blending one or more monomers selected from the group consisting of a (meth)acrylate compound represented by the general formula (1)

(wherein R$_1$ is a hydrogen atom or an alkyl group, R$_2$ is an alkylene group, and R$_3$ is an alkyl group), a (meth)acrylate compound represented by the general formula (2)

(wherein R$_4$ is a hydrogen atom or an alkyl group having 1 to 10 carbon atoms, R$_5$ is an alkylene group having 1 to 15 carbon atoms, and R$_6$ is an alkyl group having 1 to 15 carbon atoms), a (meth)acrylate compound represented by the general formula (3)

(wherein $R_7$ is a hydrogen atom or an alkyl group having 1 to 10 carbon atoms, $R_8$ is an alkylene group having 1 to 15 carbon atoms, $R_9$ is an alkylene group having 1 to 10 carbon atoms, and $R_{10}$ is an alkyl group having 1 to 15 carbon atoms), and a (meth)acrylate dimer represented by the formula (4)

2. A material for dentistry according to claim 1 which is prepared by blending said (meth)acrylate compound where said $R_1$ in said general formula (1) is an alkyl group having 1 to 10 carbon atoms, $R_2$ is a straight-chain or branched alkylene group having 1 to 15 carbon atoms, and $R_3$ is an alkyl group having 1 to 15 carbon atoms.

3. A material for dentistry according to claim 1 which is prepared by blending said monomer represented by any one of the general formulae (1) to (4) and another monomer copolymerizable with said monomer, an amount of said other monomer being 20% by weight or more with respect to the weight of both the monomers.

4. A material for dentistry according to claim 3 which is prepared by blending said monomer represented by any one of the general formulae (1) to (4), said other monomer copolymerizable with said monomer and an organic polymer which is soluble or swelling in said monomer and which has a particle diameter of 1 to 150 μm, an amount of said organic polymer being from 7.1 to 1,000 parts by weight with respect to 100 parts by weight of the total monomers.

5. A material for dentistry according to claim 3 which is prepared by blending said monomer represented by any one of said general formulae (1) to (4) and a polymerization curing agent selected from the group consisting of combinations of a peroxide and an amine, a peroxide and a sulfinic acid, and a peroxide and a cobalt compound, an amount of said polymerization curing agent being in a range of 0.01 to 15% by weight with respect to the weight of the total monomers.

6. A material for dentistry according to claim 3 which is prepared by blending said monomer represented by any one of said general formulae (1) to (4) and a photosensitizer selected from the group consisting of benzoin alkyl ethers, α-diketones and benzophenones, an amount of said photosensitizer being in a range of from 0.01 to 15% by weight with respect to the weight of said monomer.

7. A material for dentistry according to claim 3 which is prepared by blending said monomer represented by any one of said general formulae (1) to (4), said other monomer copolymerizable with said monomer, said polymerization curing agent or said photosensitizer and an inorganic filler, an amount of said inorganic filler being in a range of from 0.1 to 630 parts by weight with respect to 100 parts by weight of the total monomers.

8. A material for dentistry according to claim 1 wherein said compound represented by said general formula (1) is a compound selected from the group consisting of a compound in which $R_1$ is —$CH_3$, $R_2$ is —$CH_2CH_2$— and $R_3$ is —$CH_3$, a compound in which $R_1$ is —$CH_3$, $R_2$ is —$CH_2CH_2$— and $R_3$ is —$CH_2CH_3$, a compound in which $R_1$ is —$CH_3$, $R_2$ is —$CH_2CH_2$— and $R_3$ is —$(CH_2)_3$—$CH_3$, a compound in which $R_1$ is —$CH_3$, $R_2$ is —$CH(CH_3)$—$CH_2$— and $R_3$ is —$(CH_3)_3$—$CH_3$, a compound in which $R_1$ is —$CH_3$, $R_2$ is —$CH(CH_3)$—$CH_2$— and $R_3$ is —$CH_3$, a compound in which $R_1$ is —$CH_3$, $R_2$ is —$CH(CH_3)$—$CH_2$— and $R_3$ is —$CH_2CH_3$, a compound in which $R_1$ is —$CH_3$, $R_2$ is —$(CH_2)_4$— and $R_3$ is —$CH_2CH_3$, and a compound in which $R_1$ is —$CH_3$, $R_2$ is —$(CH_2)_6$— and $R_3$ is —$CH_2CH_3$.

9. A material for dentistry according to claim 1 wherein said compound represented by said general formula (2) is a compound selected from the group consisting of a compound in which $R_4$ is —$CH_3$, $R_5$ is —$(CH_2)_2$— and $R_6$ is —$CH_3$, a compound in which $R_4$ is —$CH_3$, $R_5$ is —$(CH_2)_2$— and $R_6$ is —$CH_2CH_3$, a compound in which $R_4$ is —$CH_3$, $R_5$ is —$(CH_2)_4$— and $R_6$ is —$CH_2CH_3$, a compound in which $R_4$ is —$CH_3$, $R_5$ is —$(CH_2)_6$— and $R_6$ is —$CH_2CH_3$, and a compound in which $R_4$ is —$CH_3$, $R_5$ is —$(CH_2)_4$ and $R_6$ is —$(CH_2)_3$—$CH_3$.

10. A material for dentistry according to claim 1 wherein said compound represented by said general formula (3) is a compound selected from the group consisting of a compound in which $R_7$ is —$CH_3$, $R_8$ is —$(CH_2)_2$—, $R_9$ is —$CH_2$— and $R_{10}$ is —$CH_3$, a compound in which $R_7$ is —$CH_3$, $R_8$ is —$(CH_2)_2$— and $R_9$ is —$(CH_2)_2$— and $R_{10}$ is —$CH_3$, a compound in which $R_7$ is —$CH_3$, $R_8$ is —$(CH_2)_4$—, $R_9$ is —$(CH_2)_2$— and $R_{10}$ is —$CH_3$, a compound in which $R_7$ is —$CH_3$, $R_8$ is —$(CH_2)_2$—, $R_9$ is —$(CH_2)_2$— and $R_{10}$ is —$CH_2CH_3$, and a compound in which $R_7$ is —$CH_3$, $R_8$ is —$(CH_2)_2$—, $R_9$ is —$(CH_2)_2$— and $R_{10}$ is —$(CH_2)_3$—$CH_3$.

11. A material for dentistry according to claim 3 wherein said other monomer copolymerizable with said monomer represented by any one of said general formulae (1) to (4) is a polyfunctional methacrylate selected from the group consisting of ethylene glycol dimethacrylate, triethylene glycol dimethacrylate, 1,6-hexanediol dimethacrylate, 2,2-bis(4-methacryloyloxyethoxyphenyl)propane, neopentyl glycol dimethacrylate and trimethylolpropane trimethacrylate.

12. A material for dentistry according to claim 4 wherein said organic polymer which is soluble or swelling in said monomer represented by any one of the general formulae (1) to (4) is a polymer selected from the group consisting of polymethyl methacrylate, polyethyl methacrylate, polybutyl methacrylate, polystyrene, methyl methacrylate/ethyl methacrylate copolymer, methyl methacrylate/butyl methacrylate copolymer, methyl methacrylate/styrene copolymer, ethyl methacrylate/butyl methacrylate copolymer, ethyl methacrylate/styrene copolymer, blended polymer compound of polymethyl methacrylate and polyethyl methacrylate, and blended polymer compound of polyethyl methacrylate and polybutyl methacrylate.

* * * * *